United States Patent [19]

Oswin et al.

[11] E Patent Number: Re. 31,915

[45] Reissued Date of Patent: Jun. 18, 1985

[54] GAS DETECTING AND MEASURING DEVICE

[75] Inventors: Harry G. Oswin, Chauncey; Keith F. Blurton, Ossining, both of N.Y.

[73] Assignee: Becton Dickinson & Company, Paramus, N.J.

[21] Appl. No.: 258,753

[22] Filed: Apr. 29, 1981

Related U.S. Patent Documents

Reissue of:

[64] Patent No.: 3,824,167
Issued: Jul. 16, 1974
Appl. No.: 172,486
Filed: Aug. 17, 1871

U.S. Applications:

[63] Continuation-in-part of Ser. No. 88,267, Nov. 10, 1970, Pat. No. 3,776,832.

[51] Int. Cl.[3] ..... G01N 27/46

[52] U.S. Cl. ..... 204/412; 204/1 T; 204/432

[58] Field of Search ..... 204/1 T, 1 N, 1 S, 1 K, 204/195 P, 195 R

[56] References Cited

U.S. PATENT DOCUMENTS

| | | | |
|---|---|---|---|
| 2,862,859 | 12/1958 | Grosskopf | 204/195 R |
| 2,898,282 | 8/1959 | Flook et al. | 204/195 R |
| 2,912,367 | 11/1959 | Asendorf et al. | 204/195 R |
| 3,028,317 | 4/1962 | Wilson et al. | 204/195 R |
| 3,103,481 | 9/1963 | Robinson | 204/195 R |
| 3,149,921 | 9/1964 | Warner | 204/1 T |
| 3,208,926 | 9/1965 | Eckfeldt | 204/195 R |
| 3,247,452 | 2/1966 | Kordesch | 204/195 R |
| 3,258,411 | 6/1966 | Hersch | 204/195 R |
| 3,275,925 | 9/1966 | Kupferberg | 204/195 R |
| 3,377,256 | 4/1968 | Sambucetti et al. | 204/195 R |
| 3,431,182 | 4/1969 | Frant | 204/195 M |
| 3,470,071 | 9/1969 | Vertes et al. | 204/195 R |
| 3,498,888 | 4/1970 | Johansson | 204/195 T |
| 3,795,589 | 5/1974 | Dahms | 204/195 P |

FOREIGN PATENT DOCUMENTS

| | | |
|---|---|---|
| 1163576 | 2/1964 | Fed. Rep. of Germany . |
| 1153551 | 3/1964 | Fed. Rep. of Germany . |
| 1202595 | 8/1970 | United Kingdom . |

OTHER PUBLICATIONS

Ives et al., "Reference Electrodes", 1961, pp. 360–378.

Mayell et al., "A Study of Surface Oxides on Platinum Electrodes", *Journal of the Electro-Chemical Society*, Apr. 1964, pp. 438–446.

Latimer, "The Oxidation States of the Elements and their Potentials in Aqueous Solutions", 2nd ed., 1952, pp. 339–348.

Grubb, "J. of the Electrochemical Society", Apr. 1964, pp. 477–478.

Muto et al., "New Methods of Microanalyzing Gases", *Analysis & Instruments*, vol. 6, No. 5, (1968), pp. 287–291.

K. A. Gresch u.a., "Die Coulometrische Analyse", Verlay Chermie, Weinheim, (1961), Seite 83, Insbe Abb 31.

W. Vielstick, "Brennstoff Element", Verlay Chermie, Weinheim, (1965), Seite 41, Insbes. Abs 3.

Hanar, "Electrode Potential Gradients and Cell Design in Controlled Potential Electrolysis Experiments", *Analytical Chemistry*, Aug. 1966, pp. 1148–1156.

*Primary Examiner*—T. Tung
*Attorney, Agent, or Firm*—Larson and Taylor

[57] ABSTRACT

A device for the detection of and quantitative measurement of a gas in a given environment, such as alcohol in the breath or carbon monoxide in the atmosphere, is described. The device comprises intake and flow control means for the gas sample, and an electrochemical cell having an anode which provides a site for electrochemical reaction of the gas being detected, a cathode, a reference electrode, and an electrolyte in contact with the anode, cathode, and reference electrode. The anode, to ensure that the current production is a result of the gas being detected and not other gases, including oxygen, is maintained at a fixed potential in relation to the potential of the reference electrode. The device provides an accurate and inexpensive means of detecting and quantitatively measuring a gas contained in a given environment, i.e., alcohol in the breath of the subject being tested or carbon monoxide in the atmosphere.

16 Claims, 10 Drawing Figures

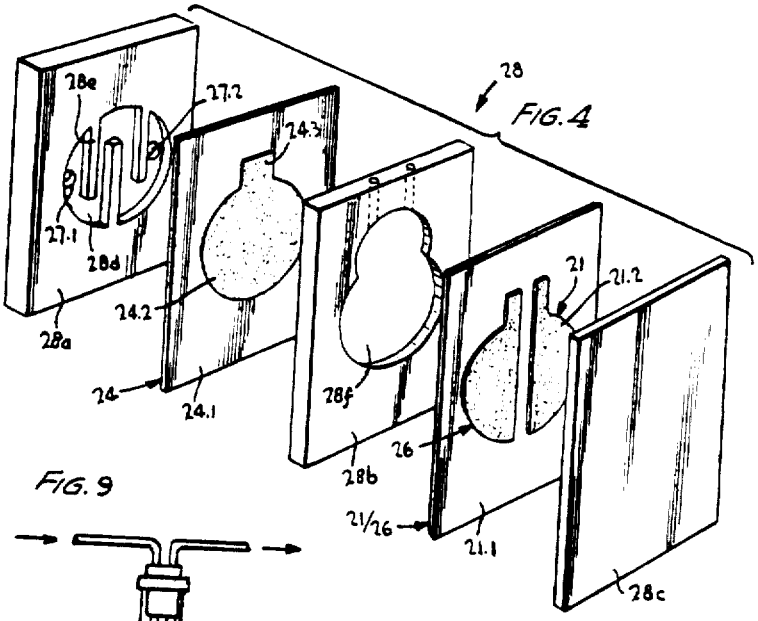
FIG. 4
FIG. 9
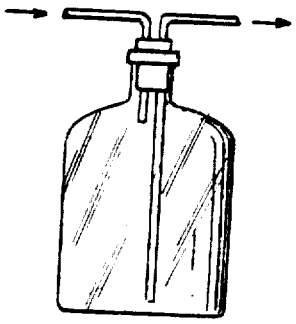
FIG. 10
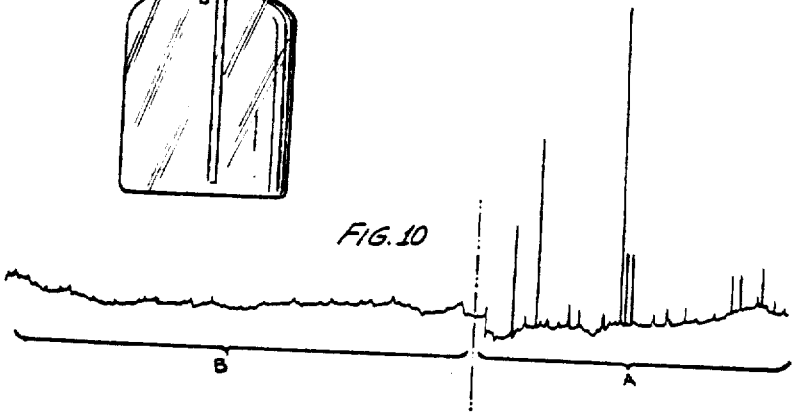

GAS DETECTING AND MEASURING DEVICE

Matter enclosed in heavy brackets [ ] appears in the original patent but forms no part of this reissue specification; matter printed in italics indicates the additions made by reissue.

This application is a continuation-in-part of our copending application U.S. Ser. No. 88,267 filed Nov. 10, 1970, now U.S. Pat. No. 3,776,832.

FIELD OF INVENTION AND BACKGROUND

This invention relates to a device for detecting and quantitatively measuring the quantity of a select gas in a gaseous medium. More particularly, the invention relates to a device which is compact, dependable, easy to operate, and relatively inexpensive for detecting and quantitatively measuring a gas such as carbon monoxide, hydrocarbons or an alcohol in an environment. The device includes intake means, means for pumping the gas being analyzed, and an electrochemical cell for detecting and quantitatively measuring a select gas. Although the invention is not limited thereto, for convenience it will be described with reference to a device for detecting and measuring the alcoholic content in the breath of a test subject or for detecting and measuring carbon monoxide in a given environment. As will be apparent, however, the device can be modified or adapted for detecting and measuring hydrocarbons including separation of saturated and unsaturated hydrocarbons, gases capable of being converted to alcohols, carbon monoxide, or hydrocarbons, or other gases which can be electro-chemically consumed, where similar conditions apply.

Alcohol Detection

Although the social problem of the drinking or drunken driver is not new, the ever-increasing number of cars on the highway and the increasing horsepower and speed of these cars is greatly enhancing the problem of the drinking or drunken driver. As a result, in the past few years insurance companies and safety groups have been publicizing this social deficiency, emphasizing the uncontestable fact that alcohol consumption on the part of drivers lead to impaired driving attitudes and habits. After the consumption of alcoholic beverages, both judgment and reaction times deteriorate, resulting in a greater probability that the driver will be involved in a car accident.

Because of the greater public awareness of the drunken or drinking driver, some states have adopted legislation aimed at the drunken driver, sometimes referred to as "driving while drinking laws," and other states are considering such laws. These laws, to be enforceable, must set objective standards as to what constitutes intoxication. Moreover, for the laws to be effective, the level of intoxication of any driver must be easily and reproducibly established—preferably at roadside—by a method which is socially acceptable, i.e., not offensive to the public as a result of the manner in which the test is conducted.

To date, the blood alcohol level is the only quantitative measurement known for determining intoxication which can be made with sufficient accuracy and which is independent of physiological and psychlogical variations from one individual to the next. Although direct quantitative tests on the whole blood are the most accurate, such tests are unsatisfactory in view of the need to take a blood sample from the test subject and the relatively complex analytical tests required to determine alcohol levels of whole blood. Although the alcohol content of urine can be correlated to the alcohol content of blood in the test subject, it is not easy to obtain a urine sample for analysis, at least not at roadside; and, moreover, the correlation of the alcohol content in urine with the alcohol content of blood requires a relatively complex analysis. Additionally, a time factor is involved in the alcohol reaching the urine after consumption of the alcohol. Therefore, most tests being considered by law enforcement and other concerned agencies are based on the alcoholic content of the test subject's breath. It is fully established that not only is alcoholic intoxication directly related to blood alcohol level, but also that the blood alcohol level and degree of a person's intoxication can be determined by the alcohol content of the test subject's breath derived from the alveolae. The alveolae are the small bulbs in the lung wherein oxidation of blood impurities take place.

Although breath tests are socially acceptable, to be fully satisfactory for use by law enforcement personnel, the breath test method employed must be (1) sufficiently accurate and reliable to ensure that a high percentage of drivers above the allowable limit and only a low percentage of those below the allowable limit will be detected and subsequently charged with drunken driving;
(2) conducted in a hygienic manner with due regard to the health and dignity of the individual driver tested;
(3) conducted with portable and easy-to-operate equipment at roadside by a law enforcement officer of only average intelligence who has no technical background or special training;
(4) rapidly carried out under all climatic conditions so that within a few minutes the apprehending officer can decide whether or not to charge the test subject with drunken driving; and
(5) low-cost, including initial cost of equipment, maintenance and operation of the equipment, and officer training costs.

Although various methods have been suggested for determining the blood alcohol level of a test subject's breath, none have met all of the aforesaid requirements. Most methods utilize chromatographic or colorimetric determinations based on the oxidation of alcohol. Such devices having sufficient accuracy, however, are not suitable for roadside checks and/or are complex and/or are expensive precluding widespread use. Moreover, presently available methods of collecting breath samples, and methods of calibrating and verifying breath samples have various deficiencies.

Carbon Monoxide Detection

The problems associated with carbon monoxide pollution and the need for carbon monoxide detectors, while being of a somewhat different nature for carbon monoxide detectors, while being of a somewhat different nature than the problem associated with the drinking driver and alcohol detection, are of no less social importance. As a result of increasing pollution, particularly in the major cities, with much of the pollution being the result of cars and other sources giving off carbon monoxide, the need for a simple and rapid means of determining and monitoring polluting gas levels in the atmosphere is critical. Although various devices are available, including infra-red detectors, chromagraphic or colorimetric devices, such units are expensive and/or slow and difficult to use as a result of establishing or adjusting to a zero line, the need to remove any water present to avoid false readings, and the like. Moreover, such devices are only marginally portable.

OBJECTS AND GENERAL DESCRIPTION OF THE INVENTION

Accordingly, a primary object of the present invention is to provide a compact, inexpensive, and easy-to-operate device for accurately and reproducibly detecting and quantitatively determining the level of a given gas in a specific environment.

Another object of this invention is to provide a compact, inexpensive, and easy-to-operate device for accurately and reproducibly detecting and quantitatively determining the blood alcohol level of a test subject from a breath sample.

It is another object of this invention to provide improved methods of collecting breath samples from a test subject which do not permit condensation of moisture in the breath and which permits the collection of substantially only olveolar breath.

Another object of this invention is to provide a breath sample collector having low energy surfaces with low heat transfer properties inhibiting the condensation of water droplets thereby increasing the accuracy of subsequent tests on the sample.

It is another object of this invention to provide a calibrator for use with blood alcohol level analyzers which is accurate, relatively inexpensive, and easy to use.

It is another object of this invention to provide a breath sample from a test subject for confirmatory analysis at a later time.

It is another object of this invention to provide a device for electrochemically detecting and quantitatively measuring the quantity of carbon monoxide in a gaseous medium.

It is another object of this invention to provide a device for electrochemically detecting and quantitatively measuring the quantity of hydrocarbon in a gaseous medium.

It is another object of this invention to provide improved composite electrodes for utilization in an electrochemical device for detecting gases in a fluid medium.

It is another object of this invention to provide electrodes for utilization in an electrochemical device which will selectively diffuse gases from a gaseous medium.

These and other objects of the present invention will be more readily apparent from the following detailed description with particular emphasis being directed to the drawings and preferred embodiments.

The aforesaid objects of the present invention are accomplished by constructing a gas detecting unit comprising in combination intake means, an electrochemical cell, means for drawing a gas through said intake means and into said electrochemical cells at a controlled flow rate, and read-out means for reading the quantity of detected gas. The electrochemical cell comprises an anode which provides a catalytic site for electrochemical reaction with the gas being detected, i.e., an alcohol, carbon monoxide, etc.; a cathode, a reference electrode, and an electrolyte in contact with an anode, cathode, and reference electrode. The anode of the cell is maintained at a fixed potential relative to the potential of the reference electrode, which is substantially free of current flow, to ensure that the current production is a result of the gas being detected and not other gases including oxygen. The fixed potential is selected within the range of from about 0.7 to 1.5 volts in order that only the gas being detected is electrochemically reacted, precluding the possibility that other gases in the sample, as well as an oxygen/water redox couple, will influence the current produced. The means for drawing gas through the intake means into the cell will effectively pass a predetermined quantity of gas to a predetermined anode surface area, thus assuring continuous accuracy in the quantitative measurement. Preferably, the quantity of gas fed to the anode surface is controlled by a constant flow control means, as will be developed more fully hereinafter, which feeds the gas sample to the electrochemical cell at a constant rate with the balance of the gas sample being vented off. Pumping or suction means are normally employed to draw the gas sample through the intake means, the electrochemical cell, and flow control means in metered amounts. Preferably the anode chamber will define a labyrinthine path through which the gas sample is passed to the anode surface. Other designs can be employed, it only being essential that the geometric anode surface area remains constant, or substantially constant, and is fed with a predetermined quantity of gas over a predetermined period of time.

In this regard it is to be noted that insofar as the actual gas being detected is concerned, it is immaterial whether the flow rate is high or low. For example, if the sample is fed to a 4 in.$^2$ electrode surface area at a low flow rate, i.e., approximately 50 cc./min., substantially all of the gas in the sample will be oxidized (greater than 95 percent). In this instance the partial pressure of the gas will be lowered substantially from the time the sample gas enters the cell to the time it exits from the cell. If the flow rate is increased to 500 cc./min., with the surface area of the electrode being maintained constant, a substantially lower percentage of the gas will be oxidized (approximately 50 percent). In this instance the lowering of the partial pressure of the sample gas between entrance of the sample into the cell and its exit will be less. If the flow rate is very high, i.e., 1500 cc./min., over the same electrode surface area, probably only about 10 percent of the gas in the sample will be oxidized. However, the partial pressure of the gas will be substantially constant between the entrance and exit of the sample from the cell. In all cases the reading obtained from the cell determines the gas content in the sample. Accordingly, it is only essential to control the flow rate of the sample and to maintain a substantially constant geometric anode surface area.

The anode of the electrochemical cell can be any anode upon which the gas is being detected, i.e., alcohol, carbon monoxide, unsaturated hydrocarbon, etc.; will electrochemically react. Preferably, however, the anode will be a lightweight electrode comprising a catalytic material such as platinum black deposited on a suitable substrate, such as unsintered polytetrafluoroethylene (PTFE), or platinum black admixed with a binder such as PTFE. The support substrate can be a plastic material such as PTFE or carbon or a metal. As will be apparent to one skilled in the art, the platinum can be replaced with other catalytic materials such as rhodium, and the like, which will effectively oxidize the gas which is being detected. The PTFE binder and/or substrate material can be replaced with other binder or substrate materials including the hydrophobic fluorocarbons such as polychlorotrifluoroethylene or the like, as well as less hydrophobic materials including polyacrylonitrile, polyvinylchloride, polyvinylalcohol, carboxymethyl cellulose, or the like. As will be further apparent to one skill in the art, when the support substrate is a hydrophobic material such as PTFE, the hydrophobic material must be oriented in the cell in order that the catalyst is in contact with the gas sample, with the catalytic layer being in contact with the electrolyte.

The specific structure of the cathode which is employed in the electrochemical cell again is not critical. It is only essential that the cathode provides a site at which oxygen will electrochemically react and withstand the corrosive environment of the electrolyte employed in the cell. The lightweight electrodes defined hereinbefore in considering the anode are preferred in view of their light weight, compactness, and stability. Their low gas diffusion resistance provides a rapid response characteristic.

The reference electrode of the electrochemical cell can be a conductive metal such as nickel, zirconium, or the like, capable of maintaining a relatively constant potential in the environment of the electrochemical cell. The third or reference electrode can be positioned between the anode and cathode, or it can be positioned behind either the anode or cathode or on the same plane or substrate as the cathode or anode. Preferably, however, in order to obtain greater compactness of the cell and due to optimum ion-transfer characteristics, and the like, the cathode and the third or reference electrode will be part of a common substrate. It is only necessary that the anode, cathode, and third electrode be electrically insulated from each other. Thus, a polymer substrate such as polytetrafluoroethylene can have two separate and distinct portions coated with a catalytic material such as platinum black, or an admixture of platinum black and PTFE particles. The entire substrate will, therefore, function as both the cathode and reference electrode. As will be more fully apparent hereinafter, various designs or lay-outs can be used.

Reference electrode, as the term is used herein, defines an electrode at which no, or substantially no, current flows. Accordingly, the reference electrode and anode must be connected through electronic circuitry, or the like, to preclude or minimize current flow between the reference electrode and working electrode, i.e., anode, so as to define and maintain a known reference potential. Although it is virtually impossible to completely eliminate current flow, the reference potential cannot show extensive drift, i.e., more than about ±25 mv.; or rapid drift, i.e., more than ±5 mv., over a period of ten seconds. If extensive or rapid drift occurs, a false reading as to the quantity of the detected gas may be obtained. As is apparent, the actual extent of current drift depends upon the accuracy of the measurement needed. If high accuracy is unnecessary, a greater current drift can be tolerated. Circuitry for the detector is set forth in applicants' aforesaid co-pending application U.S. Ser. No. 88,267.

At times it may be desirable to employ non-porous semi-permeable membranes in the fabrication of the anode in order to restrict the diffusion of gases other than the select gas being analyzed. The principle of selecting the membrane is based on solubility/diffusibility co-efficients of the various gases. For example, in detecting and quantitatively measuring alcohol, a membrane such as shellac, polyvinylalcohol, water-soluble cellulose, i.e., the cellulose ethers, esters, or ether-esters; oxyethylene, or the like, in which alcohol is soluble will be chosen. A particularly effective membrane is Edisol M manufactured and sold by Polymer Films, Inc., Woodside, N.Y., and which is methylhydroxypropyl cellulose. Another particularly effective membrane is made from dimethyl silicone polymers. Gases such as carbon monoxide and the hydrocarbons which are not soluble in the membrane would be precluded, or substantially precluded, from passage, enhancing the accuracy of the determination. Understandably, if a membrane is water-soluble, it must not be exposed to the electrolyte of the cell. This can be done by using the membranes in conjunction with hydrophobic membranes such as PTFE. As will also be understood, the selection of the membrane depends upon the gas being detected. Furthermore, in the event carbon monoxide is the gas being detected, it can be desirable to employ a scrubber, such as a carbon black or activated charcoal scrubber, between the sample intake and the electrochemical cell to remove absorbables other than water. Water is not detrimental. The scrubber can be used alone or in combination with a selective permeable membrane.

As will be fully apparent to one skilled in the art, the proper selection of anode, cathode, and reference electrode, the operating electrolyte, as well as ancillary components such as scrubbers and selectively permeable membranes will depend upon the gases which are to be analyzed and the operating conditions which must be met. The essential feature of the electrochemical cell, as pointed out hereinbefore, is in having the anode maintained at a fixed potential of from about 0.7 to 1.5 volts anodic relative to the hydrogen couple as a zero base with reference to the third or reference electrode as hereinbefore defined. Furthermore, it is necessary that the anode have a fixed geometric surface area available to the gaseous reactant which is fed at a controlled flow. This is preferably accomplished by using a labyrinthine path or by utilizing a fan for flowing the reactant gas to the electrode surface. The latter configuration is described more fully in our aforesaid co-pending application U.S. Ser. No. 88,267.

The housing of the electrochemical cell can be made of any suitable material which does not form soluble oxidizable products, preferably plastics such as the olefinic or methacrylate polymers. The housing is to be designed to permit the cathode to have an area exposed to ambient air. In view of the small quantity of air consumed, however, this can be through the electrolyte chamber or even from oxygen dissolved in the electrolyte. Moreover, as developed above, the anode must have a chamber adjacent thereto to permit controlled sample flow to the anode. The electrolyte which can be either an aqueous acid or aqueous alkaline solution can be free-flowing or trapped in a suitable matrix. In the event a matrix is employed, the matrix material must be sufficiently hydrophilic to permit continuous wetting of the anode and cathode surfaces as well as the surface of the third or reference electrode. Materials such as asbestos, Kraft paper, polyvinylalcohol, polyvinylchloride which has been treated to render it hydrophilic, or the like, can be selected.

In addition to the electrochemical cell, it is necessary that the detecting device include sample intake means and means to control the flow of the gas sample through the cell. The control of the flow rate of the sample can be accomplished in various ways. Thus, the gas sample is received through the intake means of the detecting device and pulled into the electrochemical cell, preferably by means of a suitable pump. The flow rate can be controlled in various ways including a restricted intake orifice positioned between the pump means and the intake means. In order that the test sample is received in the electrochemical cell with the minimum likelihood of water condensation in the sample and the like, the electrochemical cell is preferably positioned immediately adjacent to the sample intake with the flow meter being positioned between the pump and electrochemical cell. The flow meter and pump can be of various commercial design and form no part of the present invention. The only criterion is that the pump means have sufficient capacity to pull the gas sample through the electrochemical cell and flow meter. The flow meter must have precision sufficient to control the volume being carried through the electrochemical cell with reasonable accuracy.

When the device is used to measure the alcohol content of a test subject's breath, the sampling device, i.e., the means for collecting the breath sample, which is utilized is of substantial importance. Thus, the breath sample—for a fully accurate determination—must reach the electrochemical cell at substantially the same temperature as the test subject, i.e., approximately body temperature or 98° F. Moreover, it is important that moisture in the sample does not condense. Finally, inasmuch as the blood alcohol level is directly correlated to the breath from the alveolae, it is desirable that the sample being tested come from the alveolae and not from the mouth, throat, or trachea of the test subject. It is preferable, therefore, that the test subject thoroughly exhaust the breath from his mouth and from the throat and trachea before collecting a sample for feeding into the electrochemical cell. While it is possible to accomplish this by asking the test subject to take one or more quick breaths prior to blowing into the sample collector, under the conditions of receiving a sample, i.e., from a test subject at roadside at a time when the test subject may not be fully cooperative, it is preferable that the test sample be collected in as simple a manner as possible. In accordance with an aspect of the present invention, a sample collector is provided which comprises a long, open-ended tube having a relatively small diameter. The test subject will breathe into the sample collector with a relatively deep breath. The sample will be fed to the electrochemical cell in order that the last breath into the sample collector is the first breath out. By utilizing this method for first sample received by the electrochemical cell will be breath primarily or entirely from the alveolae providing an accurate reading of the blood alcohol level. Since the tube is open-ended, continued operation of the pump of the detecting device will exhaust and flush out the sample system and the detecting device.

Particularly in cold climates, to ensure that moisture condensation from the breath sample does not occur, it can be desirable to utilize a sample collector comprising two concentric tubes. The first and internal tube will be the open-ended tube described hereinbefore. However, a substance such as wax, Glaubers salts, or the like, which is constituted to have a melting or flow point at substantially the temperature of the test subject's body, i.e., 110° F., will be placed between the first tube and the inner walls of the second tube. The sample collector will be maintained at a temperature of 98° F., or slightly above, in order that the wax or the like will be in the fluid condition. Due to the latent heat of solidification, the entire sample collector—particularly the inner tube—will be maintained at 98° F., precluding any possibility of moisture condensation during the collection of, and analysis of the sample.

From the standpoint of legality of detection and determination of alcohol in the test subject, it is desirable that the device be quickly and accurately calibrated immediately before use. The detecting and measuring devices of the present invention permit a convenient and rapid determination of a zero or base line in contradistinction in infra-red and the like devices where it is necessary to pass nitrogen gas or some other gas which does not affect the reading through the machine to establish a zero or base line followed by feeding a gas into the device of known concentration to establish millivolts per part per million of gas. Accordingly, two separate calibrating tanks are necessary. With the present invention, the flush gas is not needed. Rather, gas flow to the device is cut off and in this way any detectable gas within the electrochemical cell is oxidized or burned off to establish its own base or zero line. Thereafter, a calibrating gas of known concentration is fed to the device to establish millivolts per part per million of gas as in infra-red or the like units. The aforesaid feature of the invention is particularly advantageous in legally determining the alcohol content in the breath of a test subject. Thus, after the detector device is operated without gas flow for a period of time, a calibrating vapor comprising a specific and predetermined ethanol content mixed with nitrogen or air is fed to the detector for a predetermined period, about 20 seconds, and the read-out of the device calibrated by adjusting the flow rate of the sample through the device or by adjusting a resistance valve in order that the predetermined reading is obtained. After the calibration and the electrochemical device is flushed by drawing in atmospheric air, the test sample will be analyzed. To ensure accuracy, it is essential that the calibrating sample be of a predetermined and consistent concentration of ethanol. This is accomplished by having the ethanol sample in a compressed gas cylinder containing air or an inert gas such as nitrogen or helium and ethanol vapor. It is important that no water vapor be in the sample. The composition of the sample is chosen in order that the partial pressure of ethanol is always less than that which would exist over pure ethanol at the lowest required operating temperature. Provided that this condition is maintained, no liquid ethanol will condense out and the sample composition will remain constant. It is essential that the calibrating test sample contain only ethanol and air or the inert gas. Water will complicate the calibration due to formation of condensate; and from the standpoint of temperature stability, i.e., at temperatures below the dew point, the concentration of the sample would vary.

It is also desirable from the standpoint of providing a legally acceptable method of determining the blood alcohol level of a test subject to provide verification means. In accordance with the present invention, this is accomplished by utilizing a sealed container having an opening at either end which can be plastic, metal, or glass, with the intake of the sealed container being in contact with a long, thin tube. The second end of the long, thin tube will be in contact with the second opening in the container, with both the inlet opening and the exit opening having a one-way valve. The test subject will breath into the verification tube in the same manner in which he breathed into the original sample collector. It may be desirable to collect the sample for immediate testing and the verification sample at the same time by having the subject breathe into a sample intake having a rotating disk which splits the breath sample into the two parts, one part being immediately analyzed and the second part being saved for verification. As with the original sample, the last breath in will be the first breath which is received by the electrochemical device and will be consistent with the original test sample analyzed at roadside. Within experimental error, the verification sample will be identical to that originally tested by the operator of the detecting device.

The final form of the detector and measuring device as hereinbefore described can vary depending upon the accuracy required in determining the blood alcohol level. For example, rather than utilizing the device for an accurate determination of the blood alcohol level, it may be desirable to merely obtain a rough indication to verify a law enforcement officer's suspicion that the test subject is under the influence of alcohol. Accordingly, the device can be designed as a sniffer-type detection unit whereby the intake of the device is merely brought within the general vicinity of the test subject. The exhaled breath of the test breath of the test subject will be brought into contact with the electrochemical device as defined hereinbefore with a reading being given of the alcoholic content of the exhaled breath. Necessarily, this method cannot be completely accurate and will be used primarily to verify or negate a police officer's suspicion that the test subject is under the influence of alcohol and will dictate or preclude requiring the test subject to undergo more accurate testing. In view of the environment of the test, i.e., in most instances at roadside where carbon monoxide is possibly present as a result of passing cars and the like, it may be desirable to filter the carbon monoxide from the sample entering the detecting device to avoid possible false readings. Accordingly, it can be desirable to include a filtering cartridge between the intake means of the detecting device and the electrochemical cell to remove carbon monoxide. The filtering cartridge can be a perm-selective membrane which will selectively pass alcohol while rejecting carbon monoxide, hydrocarbons, and the like, as discussed hereinbefore; or it can be a unit which will selectively absorb carbon monoxide. It has been found that organo-metallic compounds having the formula $MXR(P(C_2H_5)_3)_2$ wherein M is palladium, platinum, nickel, cobalt, or the like; X is a halogen or $SO_4$=radical; and R is a lower alkyl radical or an aromatic radical; or the formula $RMn(CO_5)$ wherein R is aryl or alkyl, are particularly effective in taking up carbon monoxide. Similarly, hydrocarbons, saturated and unsaturated, can be filtered by passing them through heavy oils, waxes, or the like.

The detecting device of the present invention and the nature of the ancillary components will be more readily apparent from the accompanying drawing wherein like numerals are employed to designate like parts. In the drawing:

FIG. 4 is an exploded perspective view of a second electrochemical cell useful in the detector unit;

FIG. 9 is a sump bottle for utilization with the device of FIG. 1; and

FIG. 10 is a monitoring curve, plotting the concentration of carbon monoxide in the atmosphere and the effect of the sump bottle of FIG. 9 in smoothing out the curve.

Figure 1:
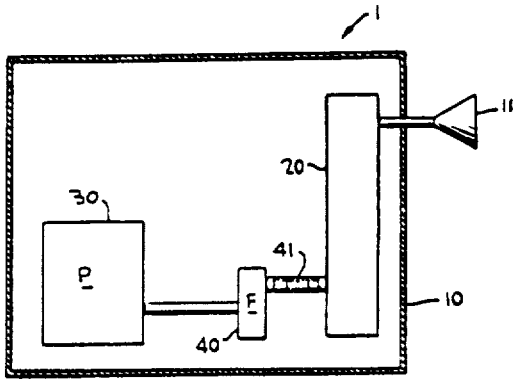
FIGS. 1 and 2 are diagrammatic views in block form of a preferred device.
Figure 2:
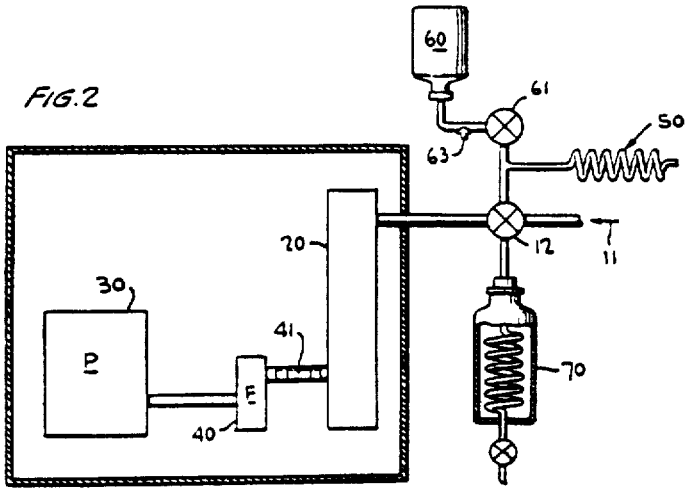

More specifically, referring to FIGS. 1 and 2, the detecting device 1 is positioned within a housing 10. The device includes a sample intake means 11 in direct communication with the electrochemical cell 20 which, in turn, is in communication with pump 30 through flow meter 40. The electronic circuitry of the device is not shown. The circuitry, however, as set forth hereinabove, is shown in applicants' co-pending application U.S. Ser. No. 88,267.

Figure 3:
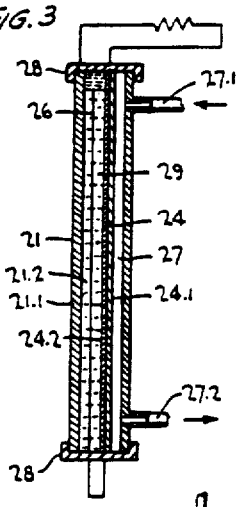
FIG. 3 is a cross-sectional view of an electrochemical cell useful in the detector unit.

The electrochemical cell, as seen most clearly from FIGS. 3 and 4, will include a cathode 21, an anode 24, and a third or reference electrode 26, all positioned within a housing 28. In the embodiment of FIG. 3, the cathode, anode, and third electrode are in contact with a free-flowing electrolyte 29. Adjacent anode 24 is reactant chamber 27 having reactant gas inlet 27.1 which is in direct communication with intake 11 and outlet 27.2 which is in communication with flow meter 40. In the embodiment shown, cathode 21 is in direct communication with atmospheric air. Both the anode and cathode are lightweight electrodes comprising a plastic substrate 24.1 and 21.1 in direct contact with reactant chamber 27 in the case of the anode, and with the ambient environment in the case of the cathode, and catalytic layers 24.2 and 21.2 which comprise a mixture of platinum black and polytetrafluoroethylene particles. The catalyst layers are in contact with the electrolyte of the cell. The platinum black is present at a loading of 10 mg./cm.$^2$. The ratio of platinum to PTFE is 10 to 7 on a weight basis. Reference electrode 26 which is in electrical contact with anode 24 is a porous, platinum coated nickel structure which is approximately 7 mils thick. A fixed potential of +1.0 volt with respect to a reversible hydrogen electrode in the same electrolyte is maintained on the anode by means of the reference electrode through a potentiostat. The anode and cathode of the cell are connected through the electrical circuit, the wiring being shown in parent application U.S. Ser. No. 88,267.

FIG. 4 shows an alternative cell wherein the housing 28 is constructed in three pieces, 28a, 28b, and 28c. 28a has a cavity 28d having holes which form gas inlets 27.1 and 27.2. A labyrinthical path is formed by vertical ribs 28e. An anode 24 comprising a polytetrafluoroethylene substrate 24.1 having a coating of platinum and PTFE particles applied as a suitable pattern 24.2 is adjacent to element 28a in order that the PTFE substrate is in contact with the reactant gas. Section 28b is adjacent to anode 24 and contains a hole 28f which serves as the electrolyte cavity. The cavity has an extension which maintains the hydrostatic head above the elecrolyte constant and serves as a reservior to accommodate any changes in volume due to environment. Additionally, air through the electrolyte contacts cathode 21 which again is on a PTFE substrate 21.1. The substrate 21.1 also serves as the base for reference electrode 26. In this manner the cell can be extremely compact. In order to show the pattern of the cathode and reference electrode, the component 21/26 is reversed. In actuality, cathode 21 and reference electrode 26 are in contact with the electrolyte of the cell. Housing element 28c forms the top of the cell and together with housing element 28a maintains the elements of the cell in operative association. Electrical leads from the cell, not shown, are fitted through the cell housing.

As noted hereinbefore, pump 30 and flow meter 40 can be any of numerous conventional units. In instances where the detector is to be employed as a portable alcohol sniffer, it may be desirable to replace the pump with a vacuum chamber which can be repeatedly evacuated by a hand piston or with an ancillary pump. Accordingly, when the device is to be used, actuation of the switch turning the device on will actuate the vacuum chamber drawing sample into the cell for detection. Furthermore, the flow meter can be replaced with a suitable restrictive orifice in instances where the accuracy of the determination is not overly critical.

Figure 8:
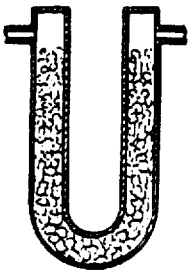
FIG. 8 is a scrubber unit for incorporation in the device of FIG. 1.

The device as shown in FIG. 1 is eminently suitable for a sniffer device for detecting alcohol in the general vicinity, or as a carbon monoxide detecting unit. In the event the device is to be used as a carbon monoxide detecting unit, preferably a scrubber will be placed between the intake 11 and electrochemical cell 20. The scrubber, as shown in FIG. 8, will comprise a U-tube containing activating carbon, charcoal, or other material which will remove condensibles such as alcohols, aldehydes, hydrocarbons, and the like; but which will not collect carbon monoxide. Accordingly, the gas entering the electrochemical cell will only be the carbon monoxide to be detected. In the event the unit is to be employed as an alcohol detector unit, and if the quantitative measurement is critical, it can be desirable to utilize a perm selective membrane in the electrochemical cell to separate the carbon monoxide which may be in the environment from the alcohol.

As seen in FIG. 2, where the device is used to detect alcohol in the breath of a test subject intake 11 is in contact with the electrochemical cell through multi-position valve 12. In a first position, air from the outside will pass through the valve directly into the cell. By turning valve 12 to a second position, intake 11 will be in communication with sample collector 50. By turning the valve to a third position, the sample collector 50 will be in direct communication with the electrochemical cell 20. By turning the valve to a fourth position, intake 11 will be in communication with verification sample collector 70. Sample collector 50 is placed in fluid communication with calibrating sample 60 by opening valve 61.

Figure 5:
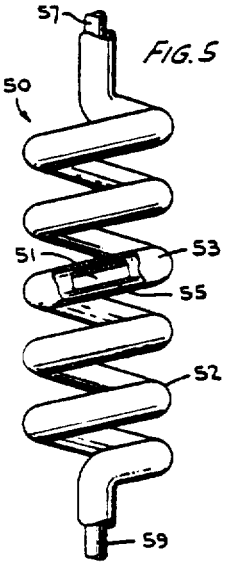
FIG. 5 is a partial cross-section of a sample collector.

The sample collector, as seen most clearly in FIG. 5, comprises an open-ended tube 51 which is surrounded with a second tube 53. The cavity between tubes 51 and 53 contains a composition 55 which is solid up to temperatures of about 98° F., but which becomes fluid or molten at about 98° F. Since the tube 51 is open-ended but of narrow diameter, gas passing into the tube will remain in the tube unless displaced by additional gas by pressure or vacuum means. Accordingly, when air is passed into the tube through first opening 57, it will progressively travel toward second opening 59.

Figure 6:
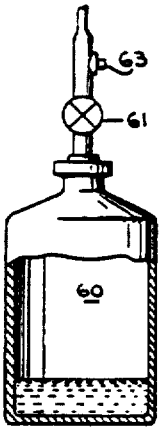
FIG. 6 is a cross-section of a calibrator bottle.

As seen in FIG. 6, calibrating device 60 is a plastic pressure bottle having a two-way valve 61 and a button 63. The bottle will contain a calibrating sample which is a mixture of nitrogen and ethanol at a predetermined concentration.

Figure 7:
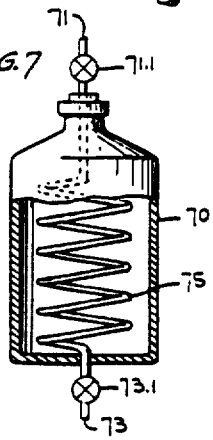
FIG. 7 is a cross-section of a verification sample collector.

As seen from FIG. 7, the verification sample bottle 70 has openings 71 and 73. These openings are connected by a continuous tube 75 of narrow diameter. As with the sample collector 50, the air passes into the tube through opening 71 and exits through opening 73. Since the sample is verification sample, it is essential that the openings 71 and 73 be closed with a one-way valve 71.1 and 73.1.

In conducting an analysis to detect and measure the blood alcohol level, the operator after selecting a test subject will actuate the detecting unit, place multi-position valve 12 in a position such that air from the environment will pass into inlet 11 and directly into the electrochemical cell. When valve 12 is in this position, valve 61 will be positioned in order that sample collector 50 is in communication with calibrating bottle 60. Actuator button 63 will be pressed to permit calibrated sample from bottle 60 to flow into and fill sample collector 50. Thereafter, valve 12 will be positioned in order that the calibrating sample from sample collector 50 is fed to cell 20. After the sample is passed into the cell, and the cell has sufficient time to reach equilibrium, i.e., a period of about 20 seconds, the detector unit will be adjusted in order that the read-out gauge, not shown, will indicate the predetermined alcohol concentration. The correcting adjustment preferably will be made by adjusting the flow rate of the sample through the cell. After the cell is calibrated, air will be drawn through open-ended sample collector 50 by merely leaving the unit running to flush the sample collector and the entire system. Thereafter, valve 12 will be positioned in order that intake 11 is in direct communication with sample collector 50. The operator will instruct the test subject to breathe into intake 11 with a breath. The breath, coming directly from the alveolae, which will be the last breath into the sample collector will be the first breath out. Valve 1 is then again positioned in order that sample collector 50 is in direct communication with the electrochemical cell and the blood alcohol level of the test subject will be read directly from the read-out gauge. In the event the blood alcohol level of the test subject is at a predetermined level, a verification sample will be collected to verify the determination by a future analysis. This is accomplished by positioning valve 12 in order that intake 11 is in direct communication with verification sample collector 70. The test subject will again be instructed to breathe into intake 11. Again the last breath in will be the first breath out of the tube when the verification sample is later analyzed to provide an accurate duplication.

The entire operation can be accomplished in less than from about three to five minutes by an operator having a minimum of technical training. The analysis including the calibration and collection of the verification sample is inexpensive since the entire unit can be used repeatedly. In view of the calibration and the collection of a verification sample, the unit provides the necessary safeguards against error. In any instance where there is an error, the error will necessarily be to the advantage of the test subject and, accordingly, the final determination is not subject to discrediting in any instances where the blood alcohol level is above the prescribed amount.

The detecting and measuring device of this invention can include various ancillary features or modifications to meet particular and specific conditions. It may be desirable, for example in order to maintain constant humidity and temperature, to thermostat the cell by including a small heating coil or the like in the device. Furthermore, when using the device to continuously monitor carbon monoxide or other gases in the environment, to avoid sharp and rapid changes due to the extreme sensitiviy of the detecting device, it can be desirable to include a sump bottle between the intake means and electrochemical cell to smooth out the plotting curve. A suitable sump bottle is shown in FIG. 9. The effect when using the sump bottle is shown in FIG. 10. In region A, the gas from the environment is fed directly to the cell. Note the sharp and quickly changing responses. In region B, the gas sample passes through the sump bottle providing a more average reading. As will be apparent, when sharp and quickly changing responses are needed, the intake means should be in direct communication with the atmosphere. However, where sharp responses are not necessary and the average and more level change is desirable, a sump pump can be useful.

Moreover, when the concentration of the gas being detected is very high, it may be difficult to obtain linearity due to swamping of the electrode with the gas sample or due to difficulty of voltage control. This can be compensated for in any of several ways:

(1) The flow of the gas can be restricted in order that the anode of the cell only receives a small amount of sample gas.

(2) A restrictive membrane can be employed. An ion-exchange membrane such as a sulphonated polystyrene ion-exchange membrane can be inserted between the working and reference electrodes to remove reactive materials. In the case of alcohol detection and measuring, this will restrict the flow of alcohols and aldehydes in the cell providing a more linear reading for the alcohol detection. Alternatively, any membrane which will restrict the flow of gases can be positioned on the gas side of the working electrode of the cell.

(3) The gas stream can be diluted with clean air at a known ratio, i.e., at a ratio of 1:1, 1:2, 1:4, or the like, in order that the anode of the electrochemical cell sees a less concentrated gas stream. This allows one to work in the concentration range which is more acceptable; for example, when determining alcohol in the blood stream above 0.12.

(4) The utilization of a reference electrode which will not oxidize or be poisoned by the gas being detected, i.e. alcohol, such as a lead oxide/lead sulphate or mercury sulphate/mercury electrode. More particularly, when a platinum/oxygen reference electrode is exposed to alcohol, this electrode will start to oxidize the alcohol and will drift in the negative direction. Therefore, the working potential will go negative. Platinum/oxygen will be reduced, causing a local cathodic current which will diminish the size of the anodic current. If this change of potential reaches the sensing electrode there will be a cathodic current, giving a lower reading for the alcohol being detected.

Further, it may be desirable to incorporate a drying capsule 41 immediately adjacent to flow meter 40. This drying capsule will collect any condensation which, for example, may be in the breath sample in the case of a BAL analysis, precluding the possibility that the condensate will interfere with the accuracy of the flow meter.

Additionally, although the present invention has been described primarily with reference to the detecting and quantitatively measuring of alcohol in the breath of a test subject, or as a carbon monoxide monitoring device, it is possible to selectively measure unsaturated hydrocarbons which are the primary smog producing hydrocarbons. Smog, according to the present understanding, is the photochemical reaction of hydrocarbons and primarily the unsaturated hydrocarbons which have greater activity to produce peroxy acids. Smog is formed from unsaturated hydrocarbons by splitting each —C=C— bond of the molecule to give two molecules of peroxy acid when oxidized. The selective measuring of unsaturated hydrocarbons can be accomplished since saturated hydrocarbons are not readily reacted at low or atmospheric temperatures. Carbon monoxide which may be present in the gas stream can be removed with selectively permeable membranes. Alcohols, if present, can be removed by passing the gas stream through a water scrubber. Furthermore, gases such as NO, $NO_2$, and $SO_2$ can be detected and measured by suitable modification of the detecting and measuring unit. These materials at the electrochemical cell undergo a change in valency state.

Moreover, in the case of detecting alcohol in the blood stream by determining the concentration of alcohol in a breath sample, an alternative arrangement to that shown in FIG. 2 would be to utilize a detector having two electrochemical cells. A gas stream which would contain alcohol vapors, and carbon monoxide in addition to air, would be split in two streams after entering the intake means with one stream being fed to cell A while the other stream is first bubbled through water prior to entering cell B. The output of cell A will consist of current derived from the oxidation of carbon monoxide and alcohol, while the output of cell B will consist only of the oxidation of carbon monoxide since the ethanol is scrubbed out in the water. By measuring the difference between the two, the output signal for alcohol can be determined. With this embodiment, selectively permeable membranes or the like are not required for the detection of alcohol even if carbon monoxide may be present, for example, with sniffer devices.

The various modifications described above are within the ability of one skilled in the art and fall within the scope of the present invention.

It is claimed:

1. A gas *device for continuously, quantitatively* detecting and measuring [unit] *a noxious gas in the presence of air* comprising in combination intake means, an electrochemical cell, means for drawing a gas through said intake means and into said electrochemical cell at a controlled flow rate, [and read-out means for reading the quantity of said detected gas,] said electrochemical cell comprising *a housing*, an anode *comprising catalyst bonded to a hydrophobic fluorocarbon membrane to provide a diffusion electrode*, a cathode, a reference electrode at which substantially no current flows, *all positioned within said housing*, and an aqueous electrolyte in an electrolyte chamber, [said electrolyte being in contact with] *each of* said anode, cathode, and reference [electrode,] *electrodes having a catalyst surface containing said electrolyte and said reference electrode contacting air*, means for exposing said anode to a gas to be detected *in the presence of air, potentiostat* means [for] maintaining said anode at a fixed potential relative to the reference electrode of from about 0.7 to 1.5 volts with respect to a reversible hydrogen electrode potential in said electrolyte of said cell, within which range oxygen reduction or oxidation of water to oxygen does not occur, [said anode comprising a catalyst bonded to a hydrophobic fluorocarbon to provide a diffusion electrode and] said catalyst *of said anode catalyst surface* catalyzing an electrochemical reaction with a gas selected from the group consisting of CO, hydrocarbons, alcohols, NO, $NO_2$ and $SO_2$ at said fixed potential, *said anode being arranged in said cell so that one surface of said anode contacts said gas exposing means and the opposite surface contacts said electrolyte whereby the noxious gas to be detected migrates from the surface contacting said exposing means to the internal surface of said anode to interface with the electrolyte for electrochemical reaction in the presence of said catalyst, means for continuously measuring said current flowing between said anode and cathode of said cell, said measured current being a measure of the concentration of the gas being detected, and read-out means for continuously reading said concentration of gas being detected.*

2. The unit of claim 1 adapted for detecting and measuring carbon monoxide and including scrubber means between said intake means and electrochemical cell for selectively collecting absorbables while permitting the gas being detected to pass through.

3. The unit of claim 2 wherein the scrubber means contains activated carbon.

4. The unit of claim 2 wherein the scrubber means contains charcoal.

5. The unit of claim 2 wherein the intake means is in communication with a sump bottle constructed and arranged with said intake means whereby gas to be detected and measured passes through said sump bottle prior to entering the electrochemical cell.

6. The unit of claim 1 wherein said means for drawing gas through said intake means and into said electrochemical cell at a controlled flow rate includes pump means and flow control means.

7. The unit of claim 6 wherein the flow control means is a restricted orifice.

8. The unit of claim 6 wherein said pump means and flow control means are constructed and arranged behind said electrochemical cell.

9. The unit of claim 1 adapted for detecting and measuring alcohol and including a selectively permeable membrane which will selectively pass alcohol while inhibiting the flow of carbon monoxide and hydrocarbons.

10. The unit of claim 9 wherein the intake means includes a multi-position valve and said valve is in controllable communication with a sample collector and the atmosphere.

11. The unit of claim 10 wherein the multi-position valve is further in communication with a verification sample collector.

12. The unit of claim 11 wherein the multi-position valve is in further communication with a calibrating sample.

13. The unit of claim 10 wherein the sample collector is an endless tube.

14. The unit of claim 1 wherein the electrochemical cell includes a composite electrode structure comprising a non-conductive base and on said non-conductive base said cathode and said reference electrode electrically separated from said cathode.

15. The unit of claim 14 wherein said electrochemical cell has a reservoir in communication with the electrolyte chamber.

16. The unit of claim 1 wherein the hydrophobic fluorocarbon is polytetrafluoroethylene.

* * * * *